United States Patent
DeRidder et al.

(10) Patent No.: US 10,850,193 B2
(45) Date of Patent: *Dec. 1, 2020

(54) UNITARILY FORMED EXPANDABLE SPINAL IMPLANT AND METHOD OF MANUFACTURING AND IMPLANTING SAME

(71) Applicant: WARSAW ORTHOPEDIC, INC., Warsaw, IN (US)

(72) Inventors: Steven DeRidder, Bartlett, TN (US); Gregory C. Marik, Collierville, TN (US); Stephen L. Ritland, Flagstaff, AZ (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/267,666

(22) Filed: Feb. 5, 2019

(65) Prior Publication Data

US 2019/0168115 A1  Jun. 6, 2019

Related U.S. Application Data

(60) Continuation of application No. 15/912,949, filed on Mar. 6, 2018, now Pat. No. 10,195,524, which is a
(Continued)

(51) Int. Cl.
*A63F 13/30* (2014.01)
*A63F 1/04* (2006.01)
(Continued)

(52) U.S. Cl.
CPC ............... *A63F 13/30* (2014.09); *A63F 1/04* (2013.01); *A63F 2001/008* (2013.01); *A63F 2009/0484* (2013.01)

(58) Field of Classification Search
None
See application file for complete search history.

(56) References Cited

U.S. PATENT DOCUMENTS

| | | |
|---|---|---|
| 4,863,476 A | 9/1989 | Shepperd |
| 5,639,070 A | 6/1997 | Deckard |

(Continued)

FOREIGN PATENT DOCUMENTS

| | | |
|---|---|---|
| CN | 104023675 A | 9/2014 |
| FR | 2753368 | 3/1998 |

OTHER PUBLICATIONS

Examination Report No. 1 dated Aug. 15, 2019 for Australian Application No. 2015378534.
(Continued)

*Primary Examiner* — Ronald Laneau

(57) ABSTRACT

A unitarily formed expandable spinal implant for insertion in a disc space between two adjacent vertebrae. The unitarily formed expandable spinal implant is moveable from an unexpanded configuration to an expanded configuration, and can be manufactured by a 3-dimensional printer. The unitarily formed expandable spinal implant includes an upper portion, a lower portion, a proximal wall, a first distal wall portion, a second distal wall portion, and a separator connected by at least one point of attachment to the spinal implant. A separation tool breaks the separator free from the at least one point of attachment, and moves the separator within the implant to force expansion thereof from the unexpanded configuration to the expanded configuration.

20 Claims, 13 Drawing Sheets

Related U.S. Application Data division of application No. 14/602,036, filed on Jan. 21, 2015, now Pat. No. 9,907,670.

(51) Int. Cl.
*A63F 1/00* (2006.01)
*A63F 9/04* (2006.01)

(56) References Cited

U.S. PATENT DOCUMENTS

| | | |
|---|---|---|
| 5,653,763 A | 8/1997 | Errico |
| 5,665,122 A | 9/1997 | Kambin |
| 6,443,989 B1 | 9/2002 | Jackson |
| 6,454,807 B1 | 9/2002 | Jackson |
| 6,491,726 B2 | 12/2002 | Ferree |
| 6,835,206 B2 | 12/2004 | Jackson |
| 7,220,280 B2 | 5/2007 | Kast et al. |
| 7,850,733 B2 | 12/2010 | Baynham et al. |
| 7,875,078 B2 | 1/2011 | Wysocki et al. |
| 7,909,869 B2 | 3/2011 | Gordon et al. |
| 8,062,375 B2 | 11/2011 | Glerum et al. |
| 8,105,358 B2 | 1/2012 | Phan |
| 8,105,382 B2 | 1/2012 | Olmos et al. |
| 8,123,810 B2 | 2/2012 | Gordon et al. |
| 8,133,232 B2 | 3/2012 | Levy et al. |
| 8,187,332 B2 | 5/2012 | Mcluen |
| 8,343,224 B2 | 1/2013 | Lynn et al. |
| 8,382,842 B2 | 2/2013 | Greenhaigh et al. |
| 8,394,145 B2 | 3/2013 | Weiman |
| 8,398,713 B2 | 3/2013 | Weiman |
| 8,403,990 B2 | 3/2013 | Dryer et al. |
| 8,435,298 B2 | 5/2013 | Weiman |
| 8,491,651 B2 | 7/2013 | Tsai |
| 8,491,657 B2 | 7/2013 | Attia et al. |
| 8,491,659 B2 | 7/2013 | Weiman |
| 8,496,706 B2 | 7/2013 | Ragab et al. |
| 8,518,120 B2 | 8/2013 | Glerum et al. |
| 8,523,944 B2 | 9/2013 | Jimenez et al. |
| 8,556,979 B2 | 10/2013 | Weiman et al. |
| 8,568,481 B2 | 10/2013 | Olmos |
| 8,628,577 B1 | 1/2014 | Jimenez |
| 8,628,578 B2 | 1/2014 | Miller et al. |
| 8,632,595 B2 | 1/2014 | Weiman |
| 8,663,329 B2 | 3/2014 | Ernst |
| 8,679,183 B2 | 3/2014 | Glerum et al. |
| 8,685,098 B2 | 4/2014 | Glerum et al. |
| 8,709,086 B2 | 4/2014 | Glerum et al. |
| 8,778,025 B2 | 7/2014 | Ragab et al. |
| 8,795,366 B2 | 8/2014 | Varela |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,926,704 B2 | 1/2015 | G!erum et al. |
| 8,940,049 B1 | 1/2015 | Jimenez |
| 9,039,771 B2 | 5/2015 | G!erum et al. |
| 9,119,730 B2 | 9/2015 | G!erum et al. |
| 10,045,824 B2 | 8/2018 | Mosnier |
| 2004/0087947 A1 | 5/2004 | Lim |
| 2005/0113916 A1 | 5/2005 | Branch |
| 2005/0131536 A1 | 6/2005 | Eisermann |
| 2006/0247770 A1 | 11/2006 | Peterman |
| 2008/0015701 A1 | 1/2008 | Garcia |
| 2008/0234822 A1 | 9/2008 | Govil |
| 2010/0145461 A1 | 6/2010 | Landry et al. |
| 2011/0054621 A1 | 3/2011 | Lim |
| 2011/0172721 A1 | 7/2011 | Varela |
| 2011/0172774 A1 | 7/2011 | Varela |
| 2012/0035729 A1 | 2/2012 | Glerum et al. |
| 2012/0109319 A1 | 5/2012 | Perisic |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2013/0144388 A1 | 6/2013 | Emery et al. |
| 2013/0158664 A1 | 6/2013 | Palmatier et al. |
| 2013/0268079 A1 | 10/2013 | Castro |
| 2014/0121774 A1 | 5/2014 | Glerum et al. |
| 2014/0277500 A1 | 9/2014 | Logan |
| 2014/0324171 A1 | 10/2014 | Glerum et al. |
| 2017/0056179 A1 | 3/2017 | Lorio |
| 2019/0365432 A1* | 12/2019 | Lee .................... A61B 17/7049 |
| 2019/0366635 A1* | 12/2019 | Holt ...................... B33Y 30/00 |
| 2020/0004225 A1* | 1/2020 | Buller .................... B33Y 50/02 |

OTHER PUBLICATIONS

Search Report from First Office Action dated Sep. 5, 2018 from Chinese Application No. CN2015800784038.6.

\* cited by examiner

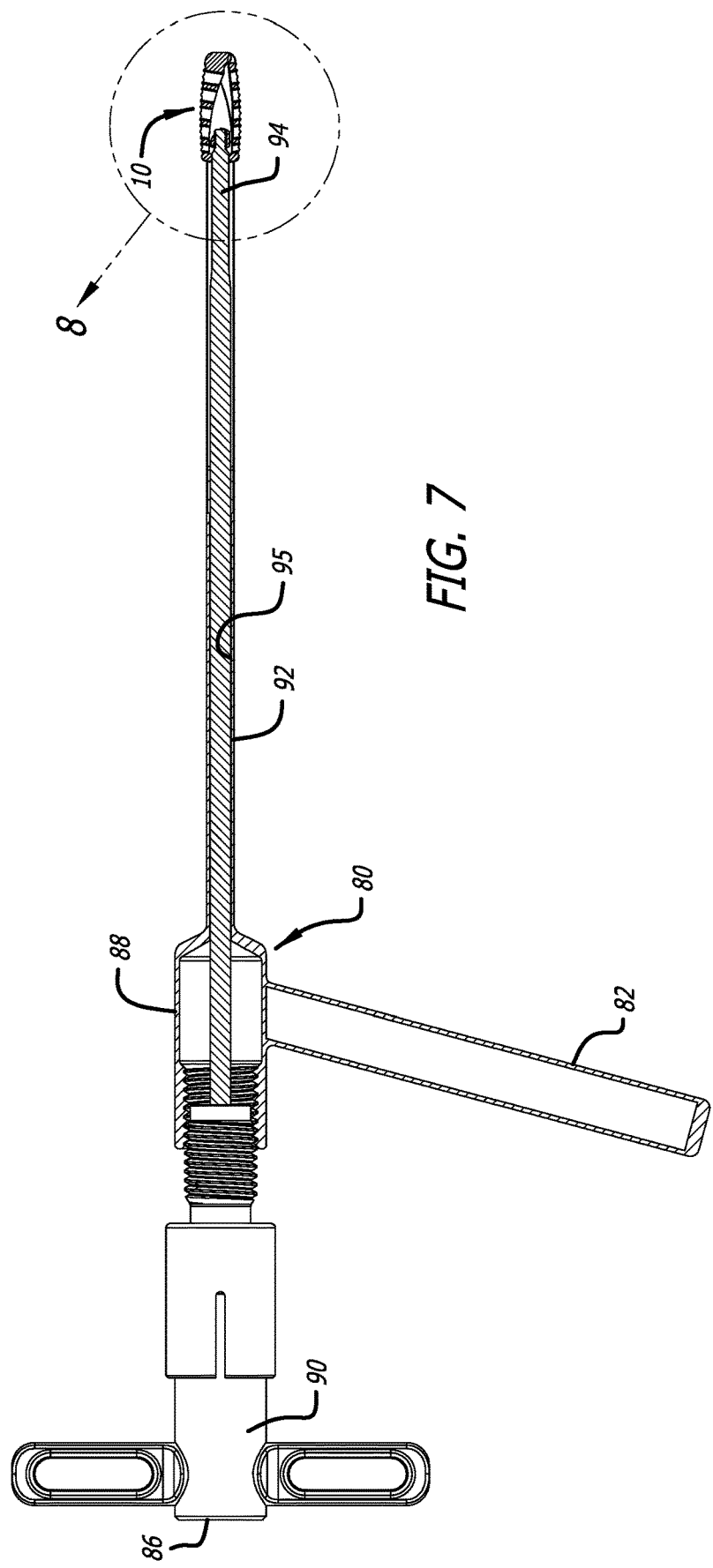

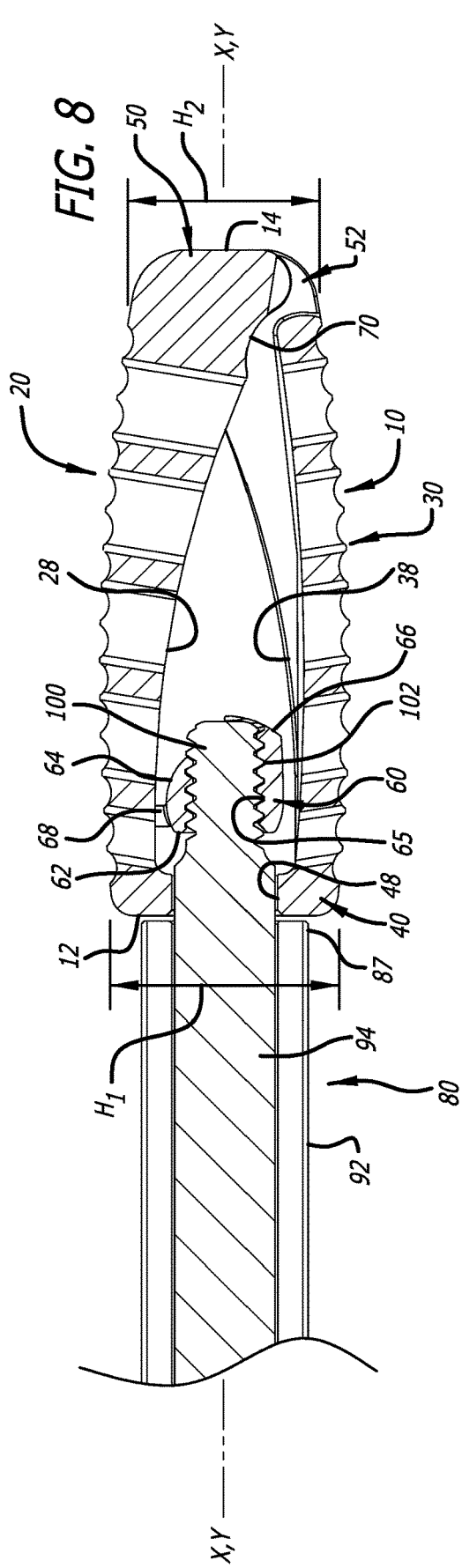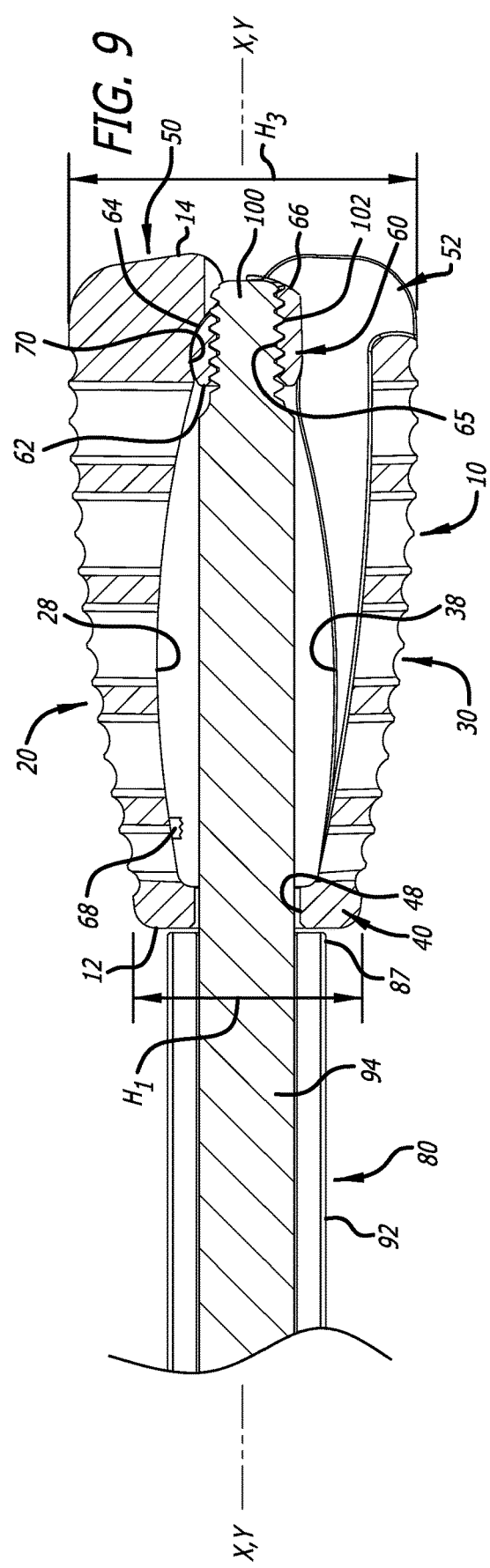

UNITARILY FORMED EXPANDABLE SPINAL IMPLANT AND METHOD OF MANUFACTURING AND IMPLANTING SAME

BACKGROUND OF THE INVENTION

The present application is a continuation of U.S. application Ser. No. 15/912,949 filed Mar. 6, 2018; which is a divisional of U.S. application Ser. No. 14/602,036 filed Jan. 21, 2015, now U.S. Pat. No. 9,907,760; all of which are incorporated by reference herein.

The present invention relates to a unitarily formed expandable spinal implant for use in spinal surgery. More particularly, the present invention relates to a unitarily formed expandable spinal implant for implantation into a disc space between two adjacent vertebrae, and movable from an unexpanded configuration to an expanded configuration. More specifically, the present invention relates to a unitarily formed expandable spinal implant including a component fixed as a unitary part thereof, which is configured, following implantation of the implant into a disc space between two adjacent vertebrae, to be broken free by an insertion tool, and moved within the implant to force expansion of the implant. The present invention further relates to a unitarily formed expandable spinal implant manufactured using a 3-dimensional printer.

DESCRIPTION OF THE RELATED ART

Expandable spinal implants are known in the art. Such expandable spinal implants can be configured to ultimately have lordotic, tapered configurations to assist in the restoration or enhancement of spinal lordosis. The expandability of such implants allows placement thereof into a corresponding surgically-enhanced disc space between two adjacent vertebrae through a relatively small surgical opening in a patient's body. Thereafter, expansion of the implants provides the advantage of increasing the heights thereof within the disc space to assist in the restoration or enhancement of spinal lordosis. The related art expandable fusion implants, however, have certain disadvantages.

The related art implants are typically manufactured with multiple parts, using traditional manufacturing methods, requiring the use of an excessive amount of material, e.g., titanium, to manufacture all of the components. For example, a significant portion of extra manufacturing material is milled away to configure the various necessary components that define the implant. The need to remove such extra manufacturing material both increases the manufacturing cost, and, for the sake of efficiency, requires the manufacture of the various components of the implants in bulk quantities.

The related art implants further are not unitarily formed expandable spinal implants configured to, after implantation into the disc space, be converted to multiple-part implants by breaking one part free from the remainder of the implant and expanding the implant with that one part.

SUMMARY OF THE INVENTION

In accordance with the invention, a unitarily formed expandable spinal implant is configured to be inserted into a disc space between two adjacent vertebrae.

The unitarily formed expandable spinal implant includes an upper portion having a proximal end and an opposite distal end, an upper portion exterior surface and an upper portion interior surface, the upper portion exterior surface and the upper portion interior surface extending from at least adjacent the proximal end to at least adjacent the distal end of the upper portion, the upper portion exterior surface configured to contact one of the two adjacent vertebrae, the upper portion interior surface at least in part declining between the upper portion proximal end and the upper portion distal end, and at least one opening being provided in the upper portion between the upper portion interior surface and the upper portion exterior surface.

The unitarily formed expandable spinal implant includes a lower portion having a proximal end and an opposite distal end, a lower portion exterior surface and a lower portion interior surface, the lower portion exterior surface and the lower portion interior surface extending from at least adjacent the proximal end to at least adjacent the distal end of the lower portion, the lower portion exterior surface configured to contact the other of the two adjacent vertebrae, the lower portion interior surface at least in part declining between the lower portion proximal end and the lower portion distal end, and at least one opening being provided in the lower portion between the lower portion interior surface and the lower portion exterior surface.

The unitarily formed expandable spinal implant further includes a chamber between portions of the upper portion and the lower portion.

The unitarily formed expandable spinal implant further includes a proximal wall having an exterior surface and an interior surface, the proximal wall extending between the upper portion and the lower portion, the proximal wall having a maximum height, and an aperture provided in the proximal wall between the interior surface and the exterior surface thereof, the aperture provided in the proximal wall communicating with the chamber.

The unitarily formed expandable spinal implant further includes a first distal wall portion and a second distal wall portion, the first distal wall portion being attached to the upper portion at the distal end thereof, the second distal wall portion being attached to the lower portion at the distal end thereof, the first distal wall portion and the second distal wall portion having a first height less than the maximum height of the proximal wall.

The unitarily formed expandable spinal implant further includes a separator having a leading portion, the separator being unitarily formed with one of the upper portion interior surface, the lower portion interior surface, and the interior surface of the proximal wall. The separator is configured to be separated by an insertion tool inserted through the aperture in the proximal wall and into contact with a trailing portion of the separator from at least one point of attachment to the remainder of the spinal implant, thereby converting the implant into a multiple-part implant. The insertion tool is further configured to force the separator toward the distal end of the spinal implant, and, in doing so, force the upper portion and the lower portion apart from one another to expand the spinal implant in the disc space into an expanded configuration, the first distal wall portion and the second distal wall portion having a second height in the expanded configuration greater than the maximum height of the proximal wall.

In accordance with another aspect of the present invention, a method of manufacturing a unitarily formed expandable spinal implant for implantation in a disc space between two adjacent vertebrae is provided. The method includes utilizing a 3-dimensional printer to lay down sequential layers of an upper portion having a proximal end and an opposite distal end, the upper portion having an upper portion exterior surface and an upper portion interior surface, the upper portion exterior surface and the upper portion interior surface extending from at least adjacent the upper portion proximal end to at least adjacent the upper portion distal end, the upper portion exterior surface being configured to contact one of the two adjacent vertebrae, the upper portion interior surface at least in part declining between the upper portion proximal end and the upper portion distal end, and at least one opening being defined between the upper portion interior surface and the upper portion exterior surface; utilizing the 3-dimensional printer to lay down sequential layers of a lower portion having a proximal end and an opposite distal end, the lower portion having a lower portion exterior surface and a lower portion interior surface, the lower portion exterior surface and the lower portion interior surface extending from at least adjacent the lower portion proximal end to at least adjacent the lower portion distal end, the lower portion exterior surface being configured to contact the other of the two adjacent vertebrae, the lower portion interior surface at least in part inclining between the lower portion proximal end and the lower portion distal end, and at least one opening being defined between the lower portion interior surface and the lower portion exterior surface; utilizing the 3-dimensional printer to lay down sequential layers of a proximal wall having an exterior surface and an interior surface, the proximal wall extending between the upper portion and the lower portion, the proximal wall having a maximum height, and an aperture provided in the proximal wall between the interior surface and the exterior surface thereof, the aperture provided in the proximal wall communicating with a chamber formed between portions of the upper portion interior surface and the lower portion interior surface; utilizing the 3-dimensional printer to lay down sequential layers of a first distal wall portion and a second distal wall portion, the first distal wall portion being attached to the upper portion at the distal end thereof, the second distal wall portion being attached to the lower portion at the distal end thereof, the first distal wall portion and the second distal wall portion having a first height less than the maximum height of the proximal wall; and utilizing the 3-dimensional printer to lay down sequential layers of a separator including a leading portion, the separator being unitarily formed with one of the upper portion interior surface, the lower portion interior surface, and the interior surface of the proximal wall by at least one point of attachment; wherein the separator is configured to be separated from the at least one point of attachment, and be moved along at least a portion of the lower portion interior surface and at least a portion of the upper portion interior surface toward the first distal wall portion and the second distal wall portion to move the upper portion and the lower portion apart from one another into an expanded configuration, the first distal wall portion and the second distal wall portion having a second height in the expanded configuration greater than the maximum height of the proximal wall.

In accordance with yet another aspect of the present invention, a method of implanting a unitarily formed expandable spinal implant into a disc space between two adjacent vertebrae is provided. The method includes utilizing the unitarily formed expandable spinal implant including: an upper portion having a proximal end, an opposite distal end, an upper portion exterior surface, and an upper portion interior surface, the upper portion exterior surface and the upper portion interior surface extending from at least adjacent the upper portion proximal end to at least adjacent the upper portion distal end, the upper portion exterior surface being configured to contact one of the two adjacent vertebrae, the upper portion interior surface at least in part declining between the upper portion proximal end and the upper portion distal end, and at least one opening being defined between the upper portion interior surface and the upper portion exterior surface; a lower portion having a proximal end, an opposite distal end, a lower portion exterior surface, and a lower portion interior surface, the lower portion exterior surface and the lower portion interior surface extending from at least adjacent the lower portion proximal end to at least adjacent the lower portion distal end, the lower portion exterior surface being configured to contact the other of the two adjacent vertebrae, the lower portion interior surface at least in part declining between the lower portion proximal end and the lower portion distal end, and at least one opening being defined between the lower portion interior surface and the lower portion exterior surface; a proximal wall having an exterior surface and an interior surface, the proximal wall extending between the upper portion and the lower portion, the proximal wall having a maximum height, and an aperture provided in the proximal wall between the interior surface and the exterior surface thereof; a chamber formed between portions of the upper portion interior surface, the lower portion interior surface, and the interior surface of the proximal wall, the aperture formed in the proximal wall communicating with the chamber; a first distal wall portion and a second distal wall portion, the first distal wall portion being attached to the upper portion at the distal end thereof, the second distal wall portion being attached to the lower portion at the distal end thereof, the first distal wall portion and the second distal wall portion having a first height less than the maximum height of the proximal wall; and a separator including a leading portion, the separator being unitarily formed with one of the upper portion interior surface, the lower portion interior surface, and the interior surface of the proximal wall by at least one point of attachment; wherein the separator is configured to be separated from the at least one point of attachment and be moved along at least a portion of the lower portion interior surface and at least a portion of the upper portion interior surface toward the first distal wall portion and the second distal wall portion to move the upper portion and the lower portion apart from one another into an expanded configuration, the first distal wall portion and the second distal wall portion having a second height in the expanded configuration greater than the maximum height of the proximal wall; inserting the spinal implant into the disc space; inserting an insertion tool through the aperture defined in the proximal wall and into contact with the separator; applying force to the separator with the insertion tool to break the at least one point of attachment; and forcing the separator along the upper portion interior surface and the lower portion interior surface toward the first distal wall portion and the second distal wall portion to move the upper portion and the lower portion apart from one another into the expanded configuration.

BRIEF DESCRIPTION OF THE DRAWINGS

The accompanying drawings, which are incorporated in and constitute a part of the specification, illustrate preferred embodiments of the invention and, together with the description, serve to explain the objects, advantages, and principles of the invention. In the drawings:

FIG. 7 is a side cross-sectional view along Line 7-7 of FIG. 4 of the spinal implant of FIGS. 1-3 and the insertion instrument of FIG. 4 attached to one another;

FIG. 8 is a side cross-sectional view enlarged from FIG. 7 showing the spinal implant of FIGS. 1-3 attached to the insertion instrument of FIG. 4 prior to expansion of the spinal implant from the unexpanded configuration to an expanded configuration using the insertion instrument to break a separator free from the remainder of the spinal implant and move the separator inside the spinal implant to facilitate expansion thereof;

FIG. 9 is a side cross-sectional view similar to FIG. 8 showing the spinal implant of FIGS. 1-3 attached to the insertion instrument of FIG. 4 after expansion of the spinal implant into the expanded configuration using the separator;

DETAILED DESCRIPTION OF THE PREFERRED EMBODIMENT

In accordance with the present invention, a first embodiment of a unitarily formed expandable spinal implant 10 is depicted in FIGS. 1-9. In accordance with the present invention, a second embodiment of a unitarily formed expandable spinal implant 110 is depicted in FIGS. 10-13, and a third embodiment of a unitarily formed expandable spinal implant 210 is depicted in FIGS. 14-17. As discussed below, each of the spinal implants 10, 110, and 210 are formed as a single part/component. Similar numerals are used to describe similar features of the unitarily formed expandable spinal implants 10, 110, and 210.

The spinal implants 10, 110, and 210 can be used as fusion implants, and are configured for placement in a disc space between two adjacent vertebrae. The spinal implants 10, 110, and 210 can be packed with fusion promoting materials to facilitate their use as spinal fusion cages. To that end, the spinal implants 10, 110, and 210 include interior cavities (or chambers) C for receiving the fusion promoting materials therein. Furthermore, as discussed below, the spinal implants 10, 110, and 210 can be moved from an unexpanded configuration to an expanded configuration. In doing so, the implants 10, 110, and 210 can be used in producing an angular relationship between the two adjacent vertebrae corresponding to naturally occurring physiologic lordosis.

Figure 1:
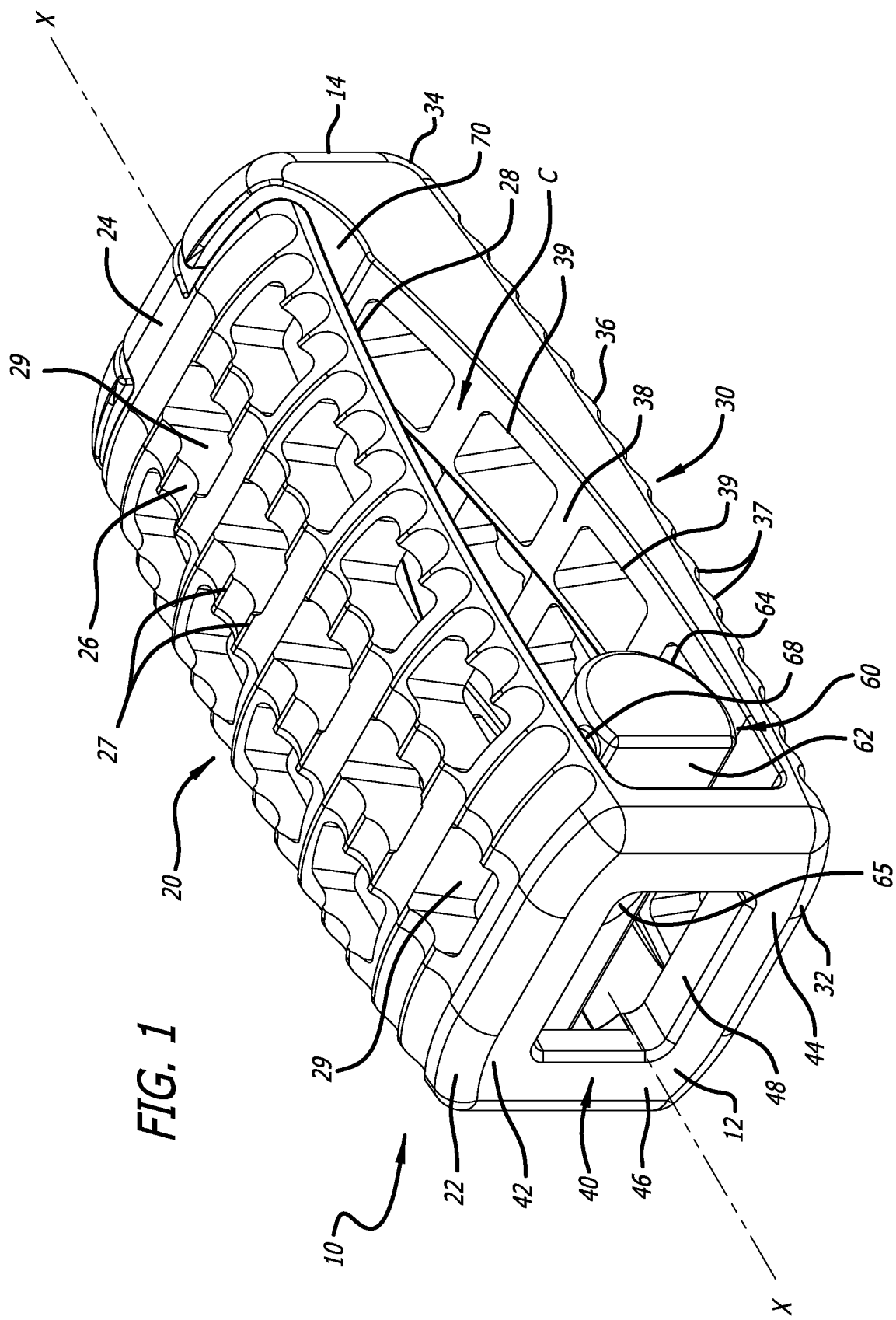
FIG. 1 is a rear perspective view of a unitarily formed expandable spinal implant in accordance with the present invention in an unexpanded configuration.
Figure 2:
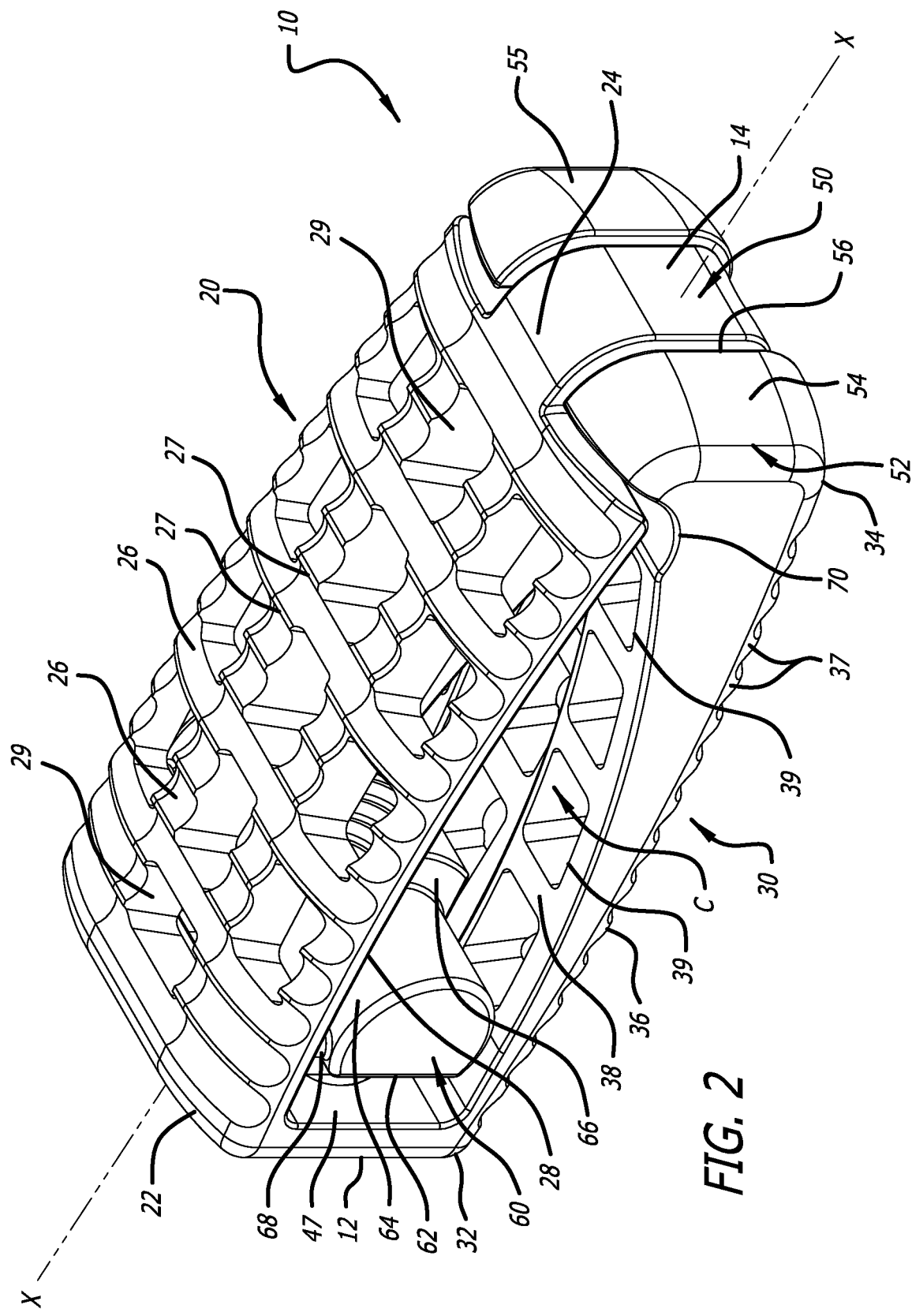
FIG. 2 is a front perspective view of the unitarily formed expandable spinal implant of FIG. 1 in the unexpanded configuration.
Figure 3:
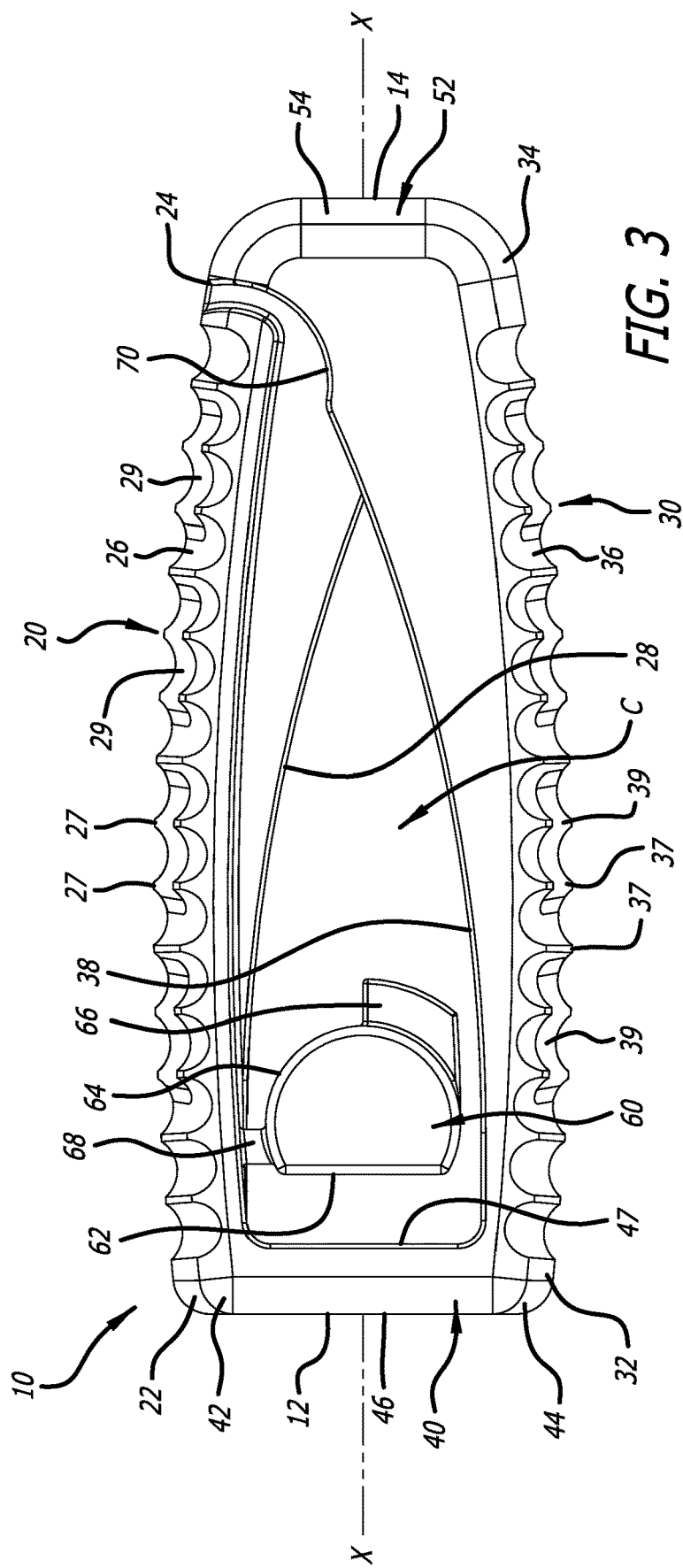
FIG. 3 is a side elevational view of the unitarily formed expandable spinal implant of FIGS. 1 and 2 in the unexpanded configuration.

As depicted in FIGS. 1-3, the spinal implant 10 includes a proximal end 12 and a distal end 14 opposite from one another, and a mid-longitudinal axis X-X extending through the proximal end 12 and the distal end 14. The spinal implant 10 includes an upper portion 20 having a proximal end 22, a distal end 24 opposite the proximal end 22, an upper portion exterior surface 26, an upper portion interior surface 28, and a plurality of apertures 29 provided between the upper portion exterior surface 26 and the upper portion interior surface 28. Furthermore, the spinal implant 10 includes a lower portion 30 having a proximal end 32, a distal end 34 opposite the proximal end 32, a lower portion exterior surface 36, a lower portion interior surface 38, and a plurality of apertures 39 provided between the lower portion exterior surface 36 and the lower portion interior surface 38.

The upper portion interior surface 28 and the lower portion interior surface 38 in part define the interior cavity (or chamber) C of the spinal implant 10. As depicted in FIG. 3, the upper portion interior surface 28 declines from adjacent the proximal end 22 to adjacent the distal end 24, and the lower portion interior surface 38 inclines from adjacent the proximal end 32 to adjacent the distal end 34. The upper portion exterior surface 26 and the lower portion exterior surface 36 can include surface roughenings 27 and 37, respectively. The surface roughenings 27 and 37 can be used to engage the adjacent vertebrae to inhibit movement of the spinal implant 10 after implantation thereof in the disc space.

As depicted in FIG. 1, the spinal implant 10 includes a proximal wall 40 at the proximal end 12 thereof. The proximal wall 40 extends between the upper portion 20 and the lower portion 30. The proximal wall 40 includes an upper edge portion 42 to which the proximal end 22 of the upper portion 20 is attached, and a lower edge portion 44 to which the proximal end 32 of the lower portion 30 is attached. The proximal wall 40 also includes an exterior surface 46 and an interior surface 47. The proximal wall 40 has a height $H_1$ (FIG. 8), and aperture 48 defined therein positioned between the upper edge 42 and the lower edge 44. The aperture 48 extends between the exterior surface 46 and the interior surface 47, and the interior surface 47 (with the upper portion interior surface 28 and the lower portion interior surface 38) in part define the interior cavity C of the spinal implant 10.

The spinal implant 10, as depicted in FIG. 2, includes a first distal wall portion 50 and a second distal wall portion 52 at the distal end 14 thereof. The first distal wall portion 50 is attached at the distal end 24 of the upper portion 20, and the second distal wall portion 52 is attached at the distal end 34 of the lower portion 30. The first distal wall portion 50 depends downwardly from the upper portion 20, and the second distal wall portion 52 depends upwardly from the lower portion 30. The second distal wall portion 52 includes side portions 54 and 55 defining a notch 56 therebetween. The notch 56 is sized to receive the first distal wall portion 50 therein when the spinal implant 10 is in the unexpanded configuration.

As depicted in FIG. 8, the first distal wall portion 50 and the second distal wall portion 52 together have a height $H_2$. The height $H_2$ corresponds to the unexpanded configuration of the spinal implant 10. The height $H_2$ is less than the height Hi of the proximal wall 40, and thus, the implant 10 has an overall tapered wedge profile in the unexpanded configuration thereof. The overall tapered wedge profile facilitates insertion of the spinal implant 10 into the disc space.

The spinal implant 10 includes a separator 60 initially attached as a unitary part of the spinal implant 10. As depicted in FIG. 8, the separator 60 is initially attached to the remainder of the spinal implant 10 proximate the proximal wall 40. For example, the separator 60 can be attached to one of the upper portion interior surface 28, the lower portion interior surface 38, and the interior surface 47 of the proximal wall 40. The separator 60 is attached to and suspended from the upper portion interior surface 28 of the upper portion 20 by at least one stem. One or more stems 68 can be used for attachment to and suspension from the upper portion interior surface 28, or alternatively or in addition thereto, one or more stems 68 can be used for attachment to and suspension of the separator 60 from the lower portion interior surface 38 and/or the interior surface 47 of the proximal wall 40.

As discussed below, the two stems 68 can be broken so that the separator 60 can be separated from the upper portion interior surface 28. Thereafter, the separator 60 can be moved along the upper portion interior surface 28 and the lower portion interior surface 38. Given the inclinations of the upper portion interior surface 28 and the lower portion interior surface 38, movement of the separator 60 towards the distal end 14 of the spinal implant 10 forces the upper portion 20 and lower portion 30 away from one another. In doing so, the spinal implant 10 can be moved from the unexpanded configuration (FIG. 8) to an expanded configuration (FIG. 9).

The separator 60 includes a trailing portion 62 and a leading portion 64. The trailing portion 62 is positioned proximate the proximal wall 40, and the leading portion 64 projects from upper and lower ends of the trailing portion 62 toward the first distal wall portion 50 and the second distal wall portion 52. As depicted in FIG. 3, the trailing portion 62 is flattened, and the leading portion 64 is partially cylindrical. Furthermore, the trailing portion 62 includes a threaded aperture 65 therein. Also as depicted in FIG. 3, an extension portion 66 projects from the leading portion 64 toward the first distal wall portion 50 and the second distal wall portion 52. The present invention, however, is not limited to a separator 60 having the above-described configuration. For example, the separators 160 and 260 used in association with the spinal implants 110 and 210, respectively, have different configurations.

As depicted in FIGS. 1, 2, 3, 8, and 9, the upper portion 20 and the lower portion 30 further include a generally concave depression 70 defined in the upper portion interior surface 28 and the lower portion interior surface 38 proximate the first distal wall portion 50 and the second distal wall portion 52. The shape of the generally concave depression 70 can be complementary to the shape of the leading portion 64 of the separator 60. As such, receipt of the leading portion 64 in the generally concave depression 70 can be used to inhibit further movement of the separator 60 toward the distal end 14 of the spinal implant 10. Furthermore, receipt of the extension portion 66 in the notch 56 between the side portions 54 and 55 of the second distal wall portion 52 can be used to inhibit side-to-side movement of the separator 60 when the leading portion 64 is received in the generally concave depression 70. Thus, the separator 60 can be moved toward the distal end 14 to move the spinal implant 10 from the unexpanded configuration to the expanded configuration, and ultimately be moved into seating engagement in the generally concave depression 70 and the notch 56 to maintain the spinal implant 10 in the expanded configuration.

As depicted in FIG. 9, the first distal wall portion 50 and the second distal wall portion 52 together have a height $H_3$. The height $H_3$ corresponds to the expanded configuration of the spinal implant 10. The height $H_3$ is greater than the height $H_1$ of the proximal wall 40. As such, the spinal implant 10 can be inserted into the disc space having an overall tapered wedge profile (unexpanded configuration), and thereafter the distal end 14 can be expanded from the height $H_2$ to the height $H_3$ to produce an angular relationship between the two adjacent vertebrae corresponding to naturally occurring physiologic lordosis.

An insertion tool 80 is provided to facilitate insertion of the spinal implant 10 into the disc space between the two adjacent vertebrae, and to facilitate expansion of the spinal implant 10 from the unexpanded configuration to the expanded configuration after insertion thereof. Furthermore, after implantation of the implant 10 into the disc space, the configuration of the insertion tool 80 affords breakage of the separator 60 from the stems 68 (which attach the separator 60 to the implant 10), and movement of the separator 60 along the upper portion interior surface 28 and the lower portion interior surface 38 toward the distal end 14 of the spinal implant 10. As discussed above, such movement of the separator 60 serves in expanding the implant 10 by forcing the upper portion 20 and the lower portion 30 apart from one another.

The insertion tool 80 includes a handle portion 82 configured to be held by a surgeon, and an operational portion 84 configured to cooperate with the separator 60. The operational portion 84 defines an axis Y-Y that is oriented generally transverse to the handle portion 82. As depicted in FIGS. 8 and 9, when the insertion tool 80 is applied to the spinal implant 10, the axis Y-Y of the operational portion 84 is generally coaxial with the axis X-X of the spinal implant 10.

Figure 4:
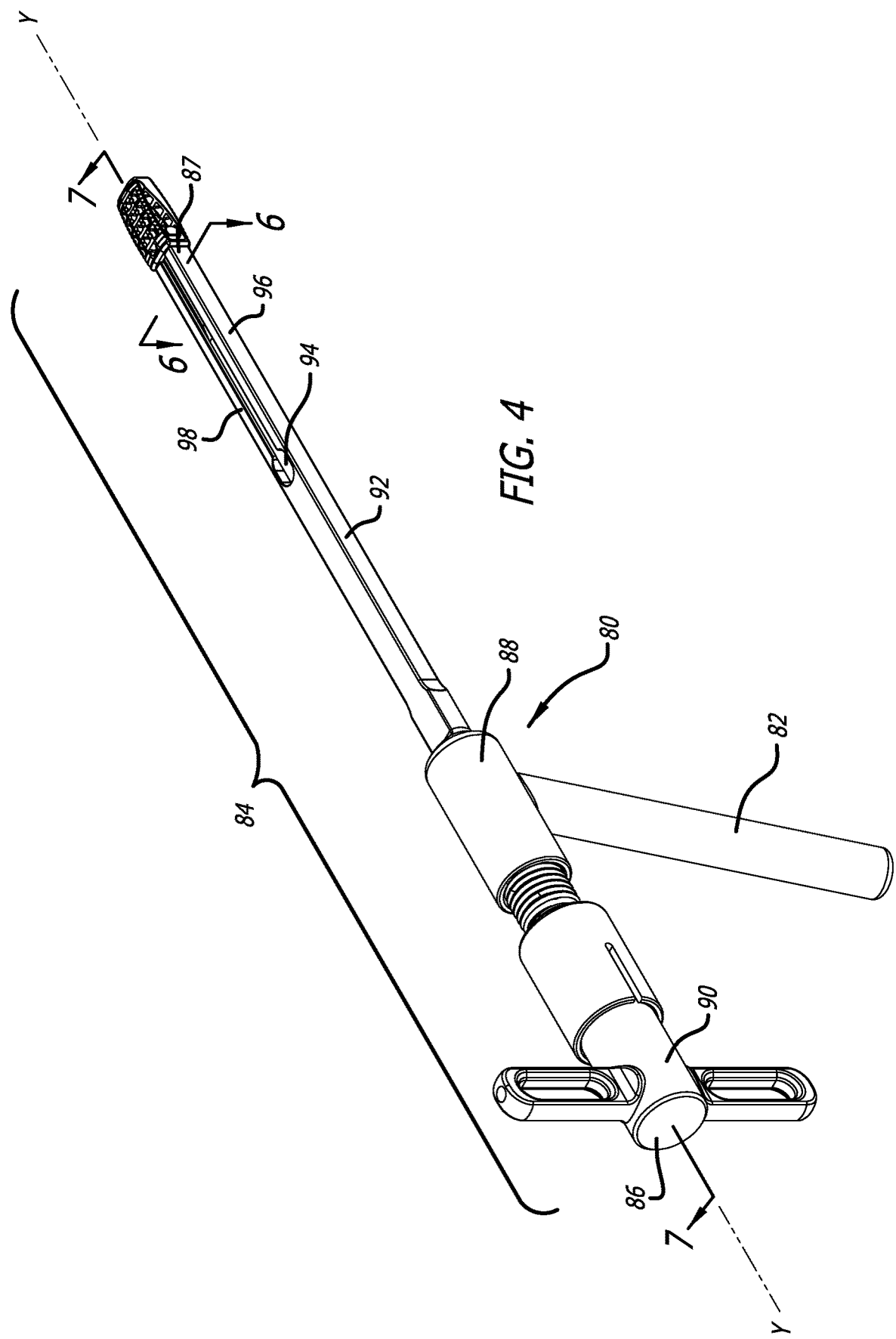
FIG. 4 is a perspective view of an insertion instrument configured to afford insertion of spinal implants in accordance with the present invention, the insertion instrument being depicted as having the spinal implant of FIGS. 1-3 attached thereto.

As depicted in FIG. 4, operational portion 84 includes a proximate end 86 and a distal end 87 opposite from one another. Furthermore, the operational portion 84 includes a body portion 88, a knob portion 90, an elongated shaft portion 92, and an elongated rod portion 94 moveable with respect to the shaft portion 92. As depicted in FIG. 4, the knob portion 90 includes the proximal end 86 and extends from the body portion 88 towards the proximal end 86, and the shaft portion 92 includes the distal end 87 and extends from the body portion 88 towards the distal end 87. The rod portion 94 extends from the body portion 88 towards the distal end 87 and is extendable beyond the distal end 87. The shaft portion 92 includes an aperture 95 for receiving the rod portion 94 therethrough that extends from the body portion 88 towards the distal end 87. Prior to inserting the knob portion 90 into the body portion 88, the rod portion 94 is advanced into engagement with the spinal implant 10 either manually or via another tool (not shown).

The shaft portion 92 is partially split along the axis Y-Y, and includes a first arm portion 96 with a first flange 97 and a second arm portion 98 with a second flange 99. The first and second flanges 97 and 99 are provided at the distal end 87 of the operational portion 84. The first and second arm portions 96 and 98 (and the first and second flanges 97 and 99) are biased toward the axis Y-Y, and the first and second flanges 97 and 99 are moveable from a disengaged position to an engaged position.

Figure 5:
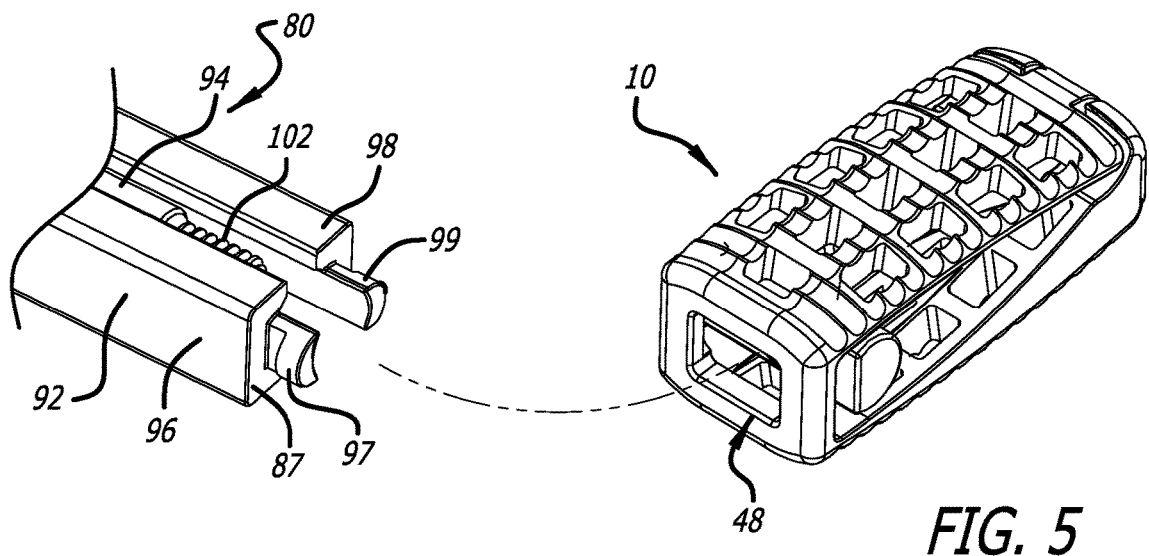
FIG. 5 is a perspective view of a leading end of the insertion instrument of FIG. 4 and a trailing end of the spinal implant of FIGS. 1-3 showing the potential for insertion of the leading end of the insertion instrument into the trailing end of the spinal implant.
Figure 6:
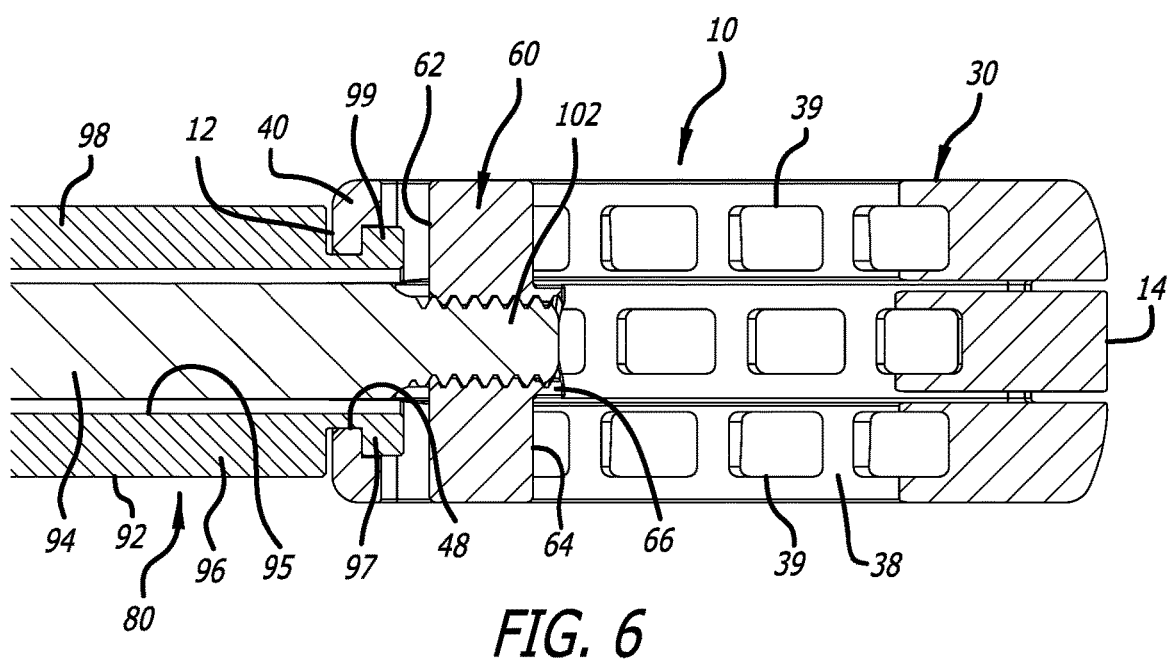
FIG. 6 is a cross-sectional view along Line 6-6 of FIG. 4 of the spinal implant of FIGS. 1-3 and the insertion instrument of FIG. 4 attached to one another.
Figure 10:
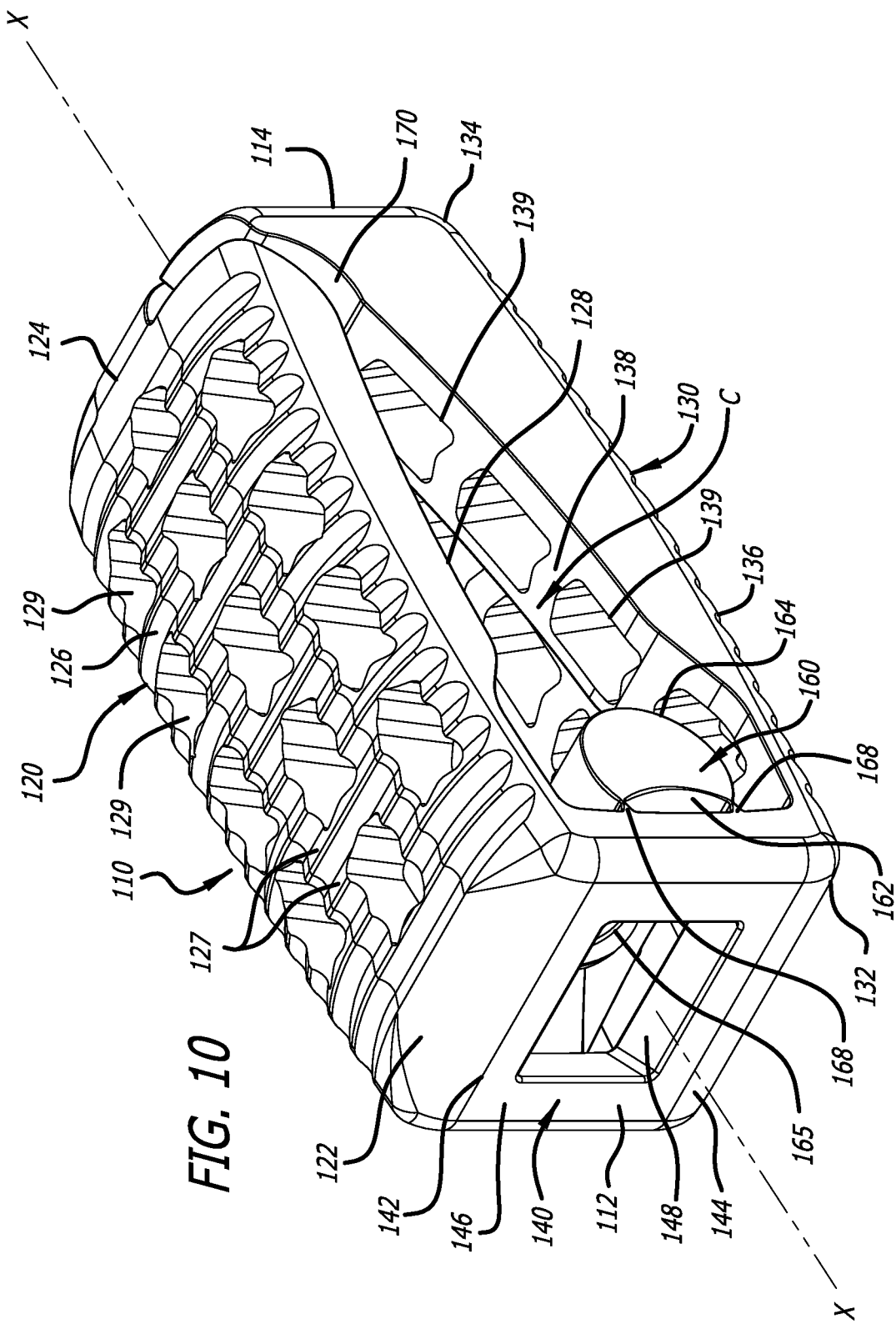
FIG. 10 is rear perspective view of another embodiment of a unitarily formed expandable spinal implant in accordance with the present invention in an unexpanded configuration.
Figure 11:
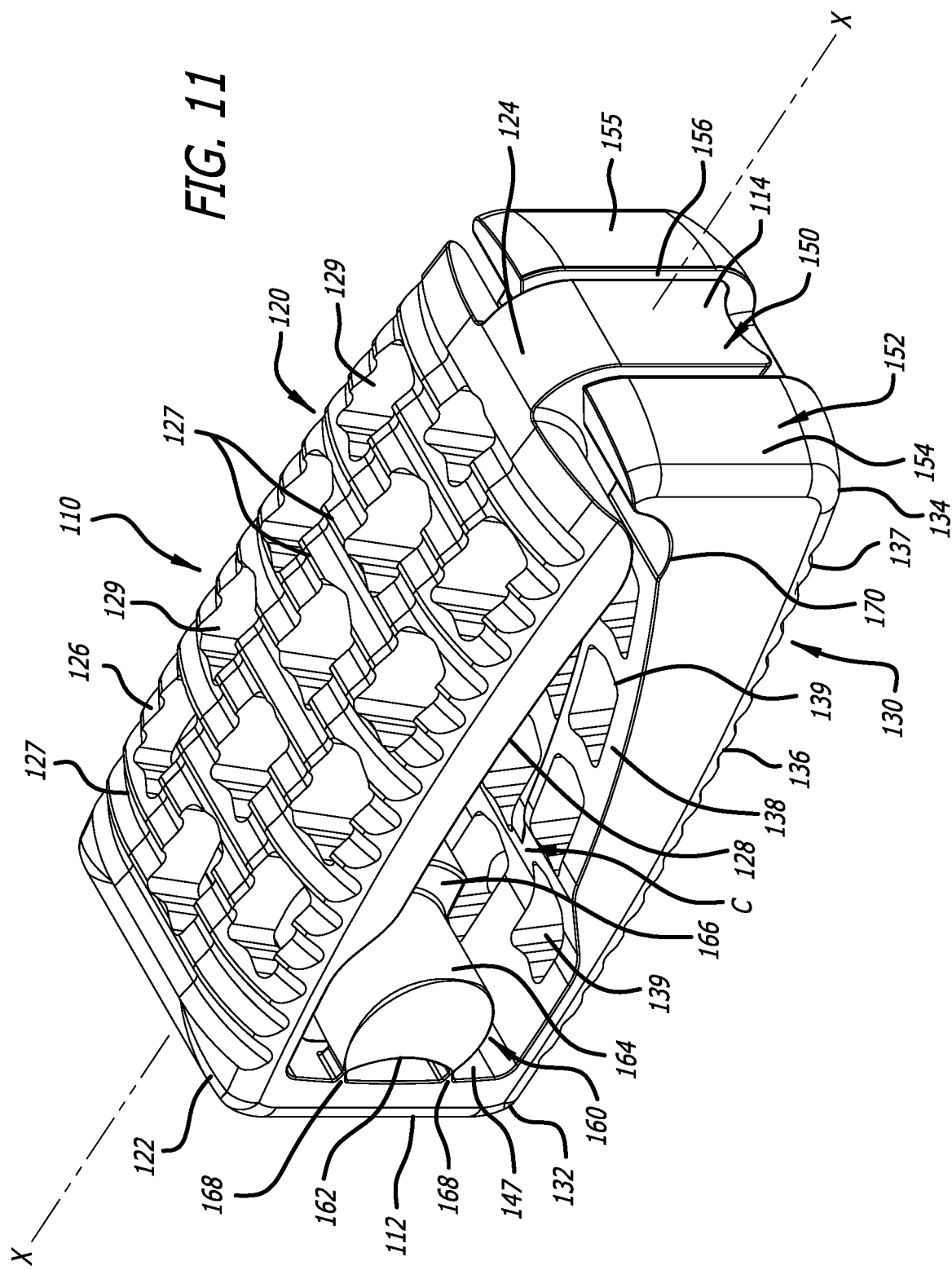
FIG. 11 is a front perspective view of the unitarily formed expandable spinal implant of FIG. 10 in the unexpanded configuration.
Figure 12:
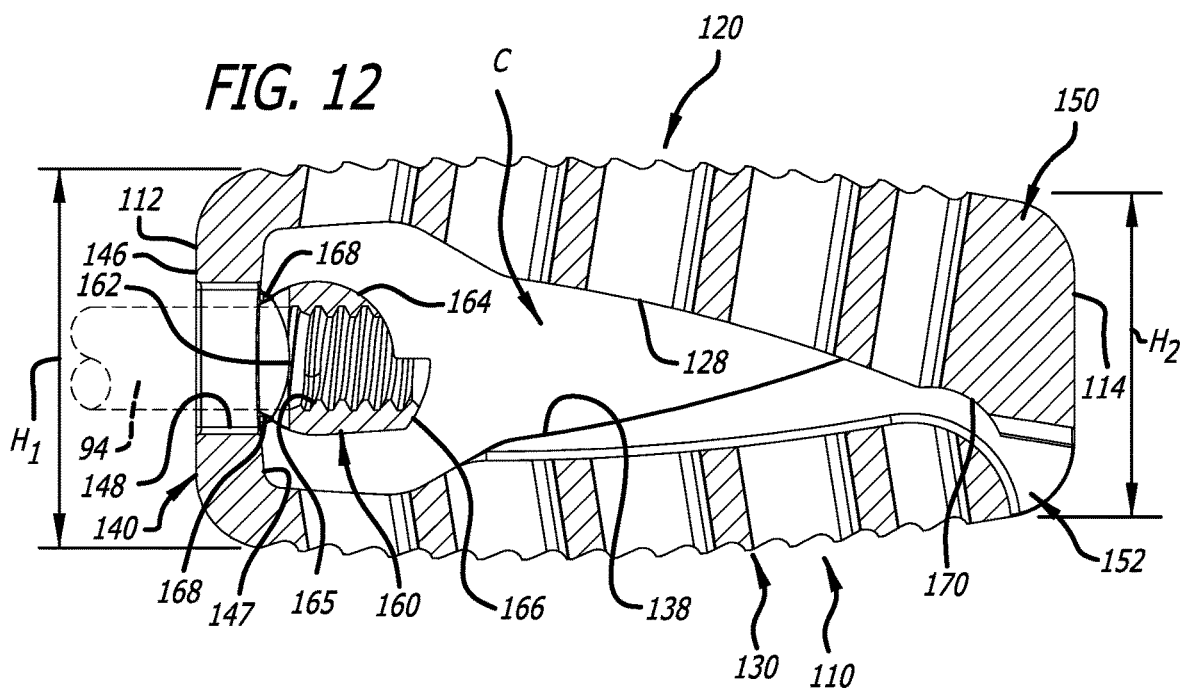
FIG. 12 is a side cross-sectional view of the spinal implant of FIGS. 10 and 11 prior to expansion of the spinal implant from the unexpanded configuration to an expanded configuration using the insertion instrument to break a separator free from the remainder of the spinal implant and move the separator inside the spinal implant to facilitate expansion thereof.

The rod portion 94 extends from the aperture 95 between the first and second arms 96 and 98 towards the distal end 87. Movement of the rod portion 94 within the shaft portion 92 towards the distal end 87 moves the two flanges 97 and 99 apart from one another. In doing so, the first and second flanges 97 and 99 can be moved from the disengaged position to the engaged position. As depicted in FIG. 5, when in the disengaged position, the first and second flanges 97 and 99 can be received through the aperture 48 formed in the proximal wall 40. Thereafter, movement of the first and second flanges 97 and 99 from the disengaged position to the engaged position serves in expanding the flanges 97 and 99 apart from one another and into contact with the sides of the aperture 48. As depicted in FIG. 6, such contact serves in holding the spinal implant 10 on the distal end 87 of the operational portion 84 of the insertion tool 80. The rod portion 94 includes an end portion 100 with threads 102 provided thereon, and the threads 102 move into engagement with the separator 60. In doing so, the end portion 100 and threads 102, as depicted in FIGS. 8 and 9, are received in the threaded aperture 65 in the trailing portion 62 of the separator 60 and rotated into engagement. As depicted in FIG. 7, with the spinal implant 10 being held by the insertion tool 80 with the knob portion 90 engaged to the body portion 88, the insertion tool 80 can be used to insert the spinal implant 10 into the disc space between the two adjacent vertebrae.

With the knob portion 90 engaged to the body portion 88, movement of the knob portion 90 serves in manipulating the rod portion 94. For example, rotation of the knob portion 90 linearly advances the rod portion 94, and movement of the knob portion 90 along axis Y-Y results in movement of the rod portion along axis Y-Y.

Further movement of the knob portion 90 can result in further motion of the rod portion 94 along axis Y-Y. Such motion of the rod portion 94 exerts pressure against the separator 60, and such pressure applied to the separator 60 can break the separator 60 free from its attachment to the remainder of the spinal implant 10. For example, such pressure can break the two stems 68 to release the separator 60 from its attachment to and suspension from the upper portion interior surface 28. Once separated from the remainder of the spinal implant 10, the separator 60 can be moved by the rod portion 94 (via movement of the knob portion 90) along the upper portion of interior surface 28 and the lower portion of interior surface 38 toward the distal end 14. As discussed above, such movement forces the upper portion 20 and lower portion 30 away from one another, so that the spinal implant 10 can be moved from the unexpanded configuration (FIG. 8) to an expanded configuration (FIG. 9). Ultimately, the separator 60 is moved by the rod portion 94 into seating engagement in the generally concave depression 70 and the notch 56 to maintain the spinal implant 10 in the expanded configuration.

After the spinal implant 10 has been implanted, moved from the unexpanded position to the expanded position via movement of the separator 60, and the insertion tool 80 is detached from the spinal implant 10, the interior cavity C can be packed with fusion promoting materials to facilitate its use as a spinal fusion cage. For example, the fusion promoting materials can be inserted through the aperture 48 in the proximal wall 40 into the interior cavity C.

Figure 13:
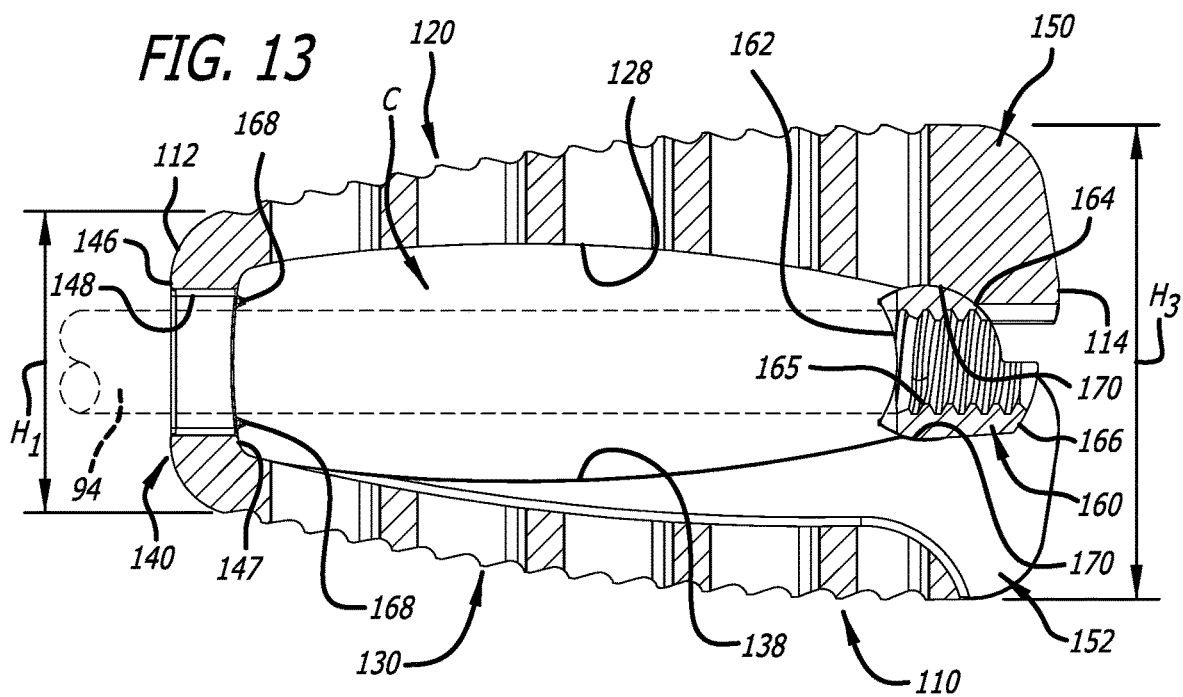
FIG. 13 is a side cross-sectional view similar to FIG. 12 showing the spinal implant of FIGS. 10 and 11 after expansion thereof into the expanded configuration using the separator.
Figure 14:
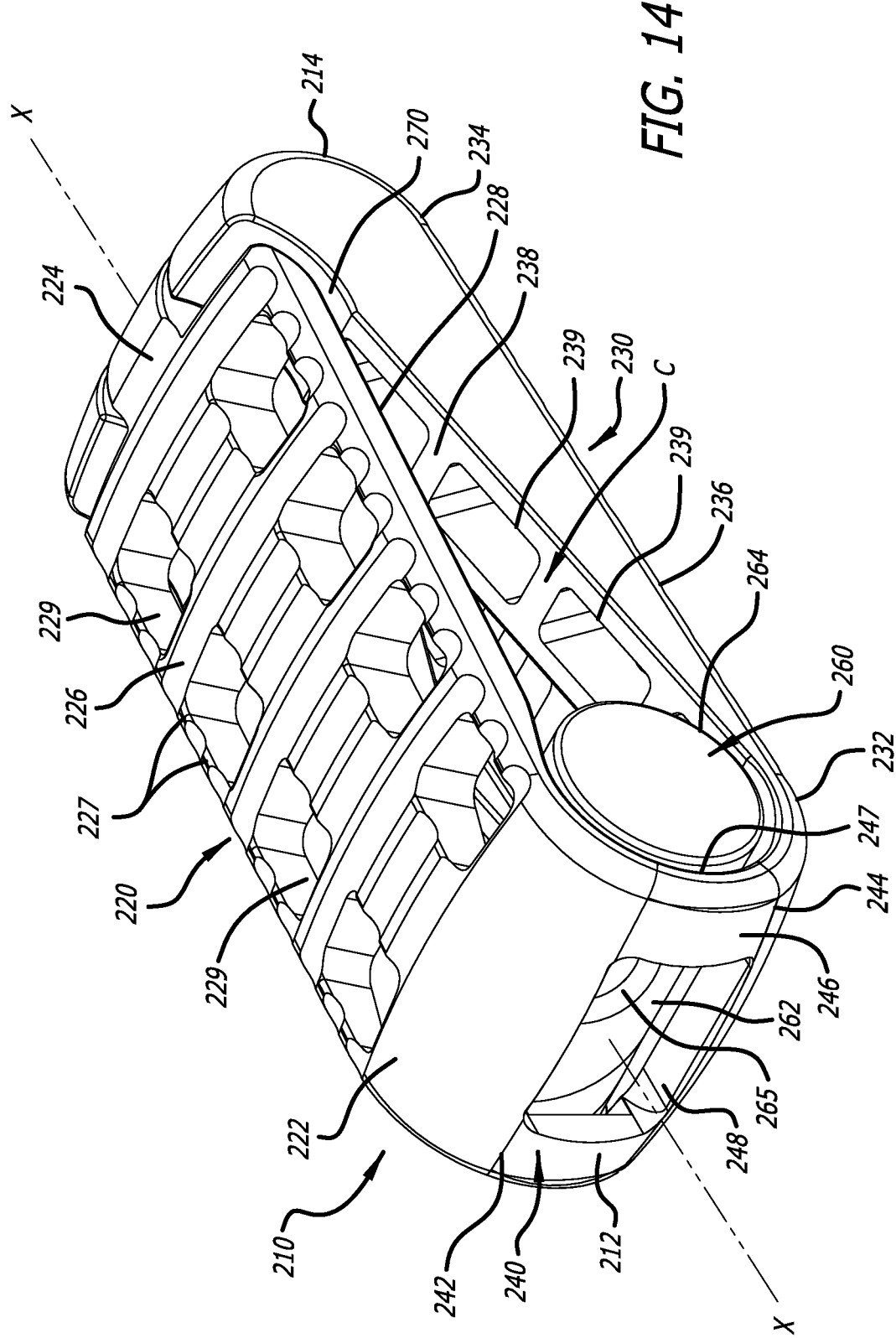
FIG. 14 is a rear perspective view of yet another embodiment of a unitarily formed expandable spinal implant in accordance with the present invention in an unexpanded configuration.
Figure 15:
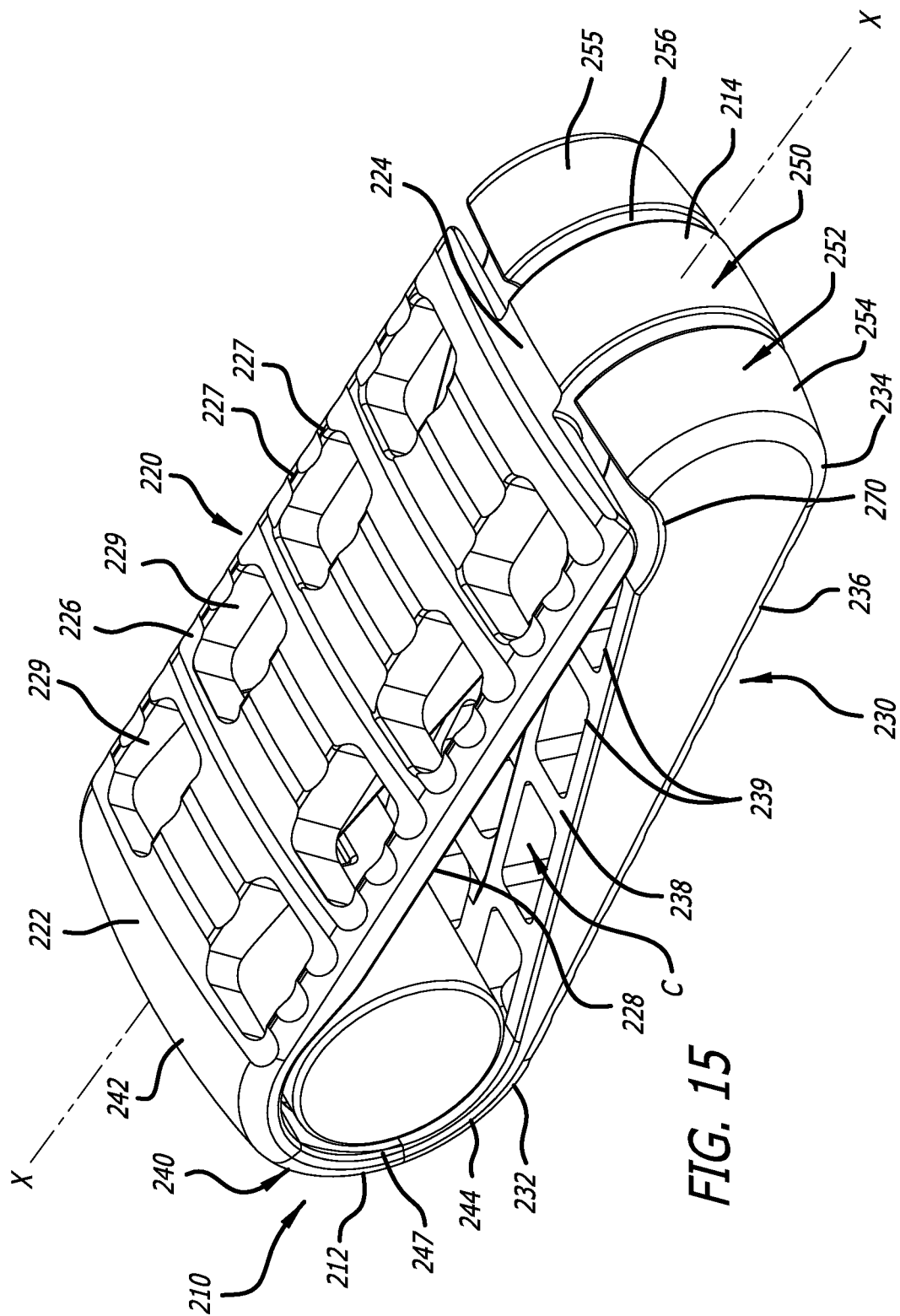
FIG. 15 is a front perspective view of the unitarily formed expandable spinal implant of FIG. 14 in the unexpanded configuration.
Figure 16:
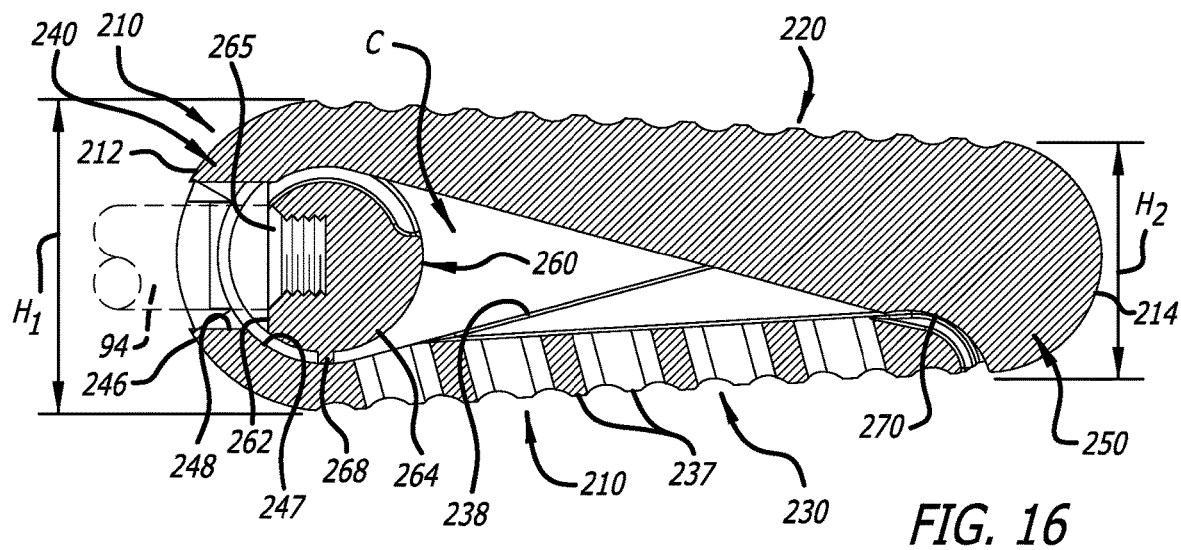
FIG. 16 is a side cross-sectional view of the spinal implant of FIGS. 14 and 15 prior to expansion of the spinal implant from the unexpanded configuration to an expanded configuration using the insertion instrument to break a separator free from the remainder of the spinal implant and move the separator inside the spinal implant to facilitate expansion thereof.
Figure 17:
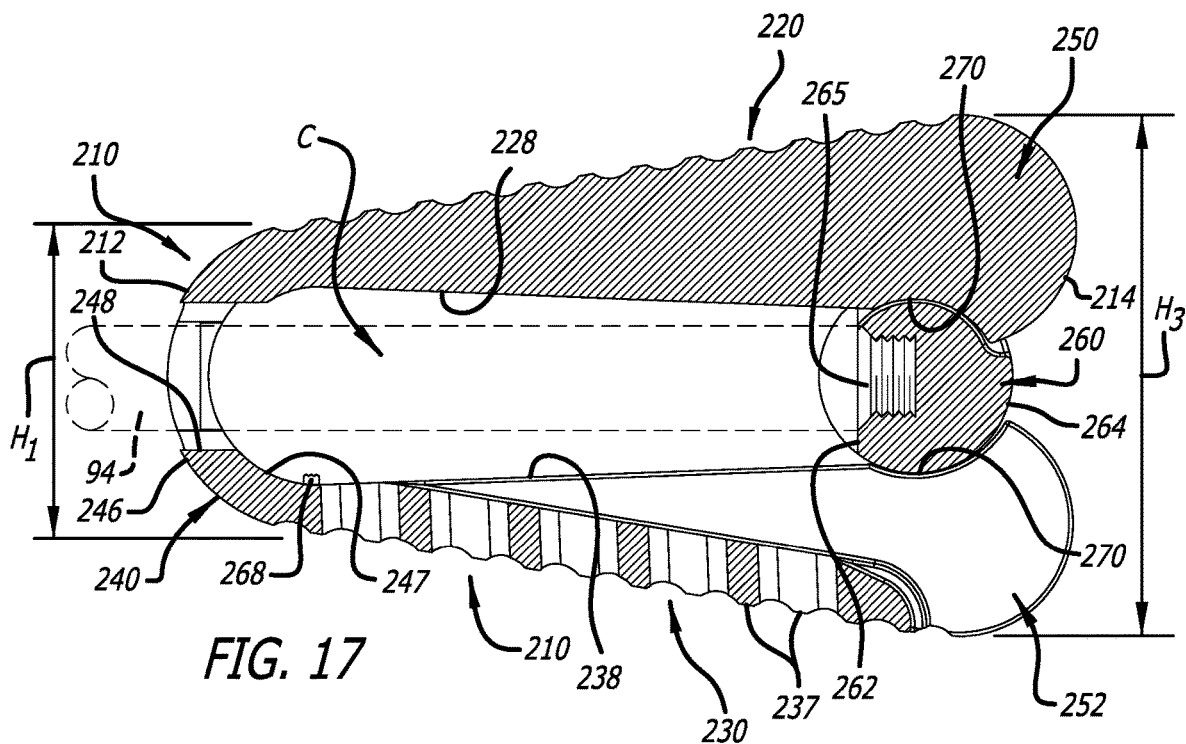
FIG. 17 is a side cross-sectional view similar to FIG. 16 showing the spinal implant of FIGS. 14 and 15 after expansion thereof into the expanded configuration using the separator.

As discussed above, the second embodiment of a unitarily formed expandable spinal implant 110 is depicted in FIGS. 10-13, and the third embodiment of a unitarily formed expandable spinal implant 210 is depicted in FIGS. 14-17. Numerals similar to those used to describe the features of the spinal implant 10 are also used to describe the features of the spinal implants 110 and 210. Like the spinal implant 10, the spinal implants 110 and 210 can be moved from an unexpanded configuration (FIGS. 12 and 16) to an expanded configuration (FIGS. 13 and 17).

The present invention further includes a method of manufacturing the unitarily formed expandable spinal implants 10, 110, and 210 having the structural features described above using a 3-dimensional printer. The method includes forming sequential layers of each of the above-described components of the unitarily formed expandable spinal implants 10, 110, and 210 by selectively sintering layers of titanium powder, with a laser, to create sequential layers of each component. The titanium powder is applied, and successive layers sintered, until each respective complete component, and eventually the complete unitarily formed expandable spinal implants 10, 110, and 210, configured as disclosed above, is manufactured. Preferably, the titanium powder is provided by a powder dispensing mechanism, and the laser is controlled by a computer, preprogrammed with CAD data depicting the configuration of each part of the unitarily formed expandable spinal implants 10, 110, and 210, as described above. One complete exemplary description of the manufacturing process used by the 3-dimensional printer is disclosed in U.S. Pat. No. 5,639,070, the contents of which are incorporated herein by reference.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of manufacturing a unitarily formed expandable spinal implant for implantation in a disc space between two adjacent vertebrae, the method comprising:

utilizing a 3-dimensional printer to lay down sequential layers of an upper portion having a proximal end and an opposite distal end, the upper portion having an upper portion exterior surface and an upper portion interior surface, the upper portion exterior surface and the upper portion interior surface extending from at least adjacent the upper portion proximal end to at least adjacent the upper portion distal end, the upper portion exterior surface being configured to contact one of the two adjacent vertebrae;

utilizing the 3-dimensional printer to lay down sequential layers of a lower portion having a proximal end and an opposite distal end, the lower portion having a lower portion exterior surface and a lower portion interior surface, the lower portion exterior surface and the lower portion interior surface extending from at least adjacent the lower portion proximal end to at least adjacent the lower portion distal end, the lower portion exterior surface being configured to contact the other of the two adjacent vertebrae;

utilizing the 3-dimensional printer to lay down sequential layers of a proximal wall having an exterior surface and an interior surface, the proximal wall extending between the upper portion and the lower portion, the proximal wall having a maximum height, and an aperture provided in the proximal wall between the interior surface and the exterior surface thereof, the aperture provided in the proximal wall communicating with a chamber formed between portions of the upper portion interior surface and the lower portion interior surface; and utilizing the 3-dimensional printer to lay down sequential layers of a separator including a leading portion, the separator being unitarily formed with one of the upper portion interior surface, the lower portion interior surface, and the interior surface of the proximal wall by at least one point of attachment;

wherein the separator is configured to be separated from the at least one point of attachment, and be moved along at least a portion of the lower portion interior surface and at least a portion of the upper portion interior surface away from the proximal wall to move the upper portion and the lower portion apart from one another into an expanded configuration, a height in the expanded configuration measured away from the proximal wall being greater than the maximum height of the proximal wall.

2. The method of claim 1, wherein titanium powder is used with the 3-dimensional printer to manufacture the unitarily formed expandable spinal implant.

3. The method of claim 1, further comprising utilizing the 3-dimensional printer to lay down sequential layers of an insertion tool configured to separate the separator from the at least one point of attachment and move the separator along the portions of the lower portion interior surface and the upper portion interior surface.

4. The method of claim 1, further comprising utilizing the 3-dimensional printer to define at least one opening between the upper portion interior surface and the upper portion exterior surface.

5. The method of claim 1, further comprising utilizing the 3-dimensional printer to define at least one opening between the lower portion interior surface and the lower portion exterior surface.

6. The method of claim 1, wherein the separator is separably attached to the one of the upper portion interior surface, the lower portion interior surface, and the interior surface of the proximal wall by at least one point of attachment.

7. The method of claim 6, further comprising providing an insertion tool configured to be inserted through the aperture in the proximal wall, and into contact with the separator to break the separator free from the at least one point of attachment, and move the separator away from the proximal wall.

8. The method of claim 7, wherein the separator includes an aperture, and the insertion tool includes a distal end configured to fit into the aperture of the separator.

9. The method of claim 1, wherein the upper portion interior surface includes a concave portion, and the lower portion interior surface includes a concave portion.

10. The method of claim 9, wherein the concave portions of the upper portion interior surface and the lower portion interior surface are configured to receive therein portions of the separator, the concave portions inhibiting further movement of the separator along the lower portion interior surface and the upper portion interior surface.

11. The method of claim 1, wherein at least a portion of the chamber between the upper portion and the lower portion is configured to receive bone growth material therein.

12. A method of manufacturing a unitarily formed expandable spinal implant for implantation in a disc space between two adjacent vertebrae, the method comprising:

utilizing a 3-dimensional printer to lay down sequential layers of an upper portion having a proximal end and an opposite distal end, the upper portion having an upper portion exterior surface and an upper portion interior surface, the upper portion exterior surface and the upper portion interior surface extending from at least adjacent the upper portion proximal end to at least adjacent the upper portion distal end;

utilizing the 3-dimensional printer to lay down sequential layers of a lower portion having a proximal end and an opposite distal end, the lower portion having a lower portion exterior surface and a lower portion interior surface, the lower portion exterior surface and the lower portion interior surface extending from at least adjacent the lower portion proximal end to at least adjacent the lower portion distal end;

utilizing the 3-dimensional printer to lay down sequential layers of a proximal wall having an exterior surface and an interior surface, the proximal wall extending between the upper portion and the lower portion, the proximal wall having a maximum height, and an aperture provided in the proximal wall between the interior surface and the exterior surface thereof, the aperture provided in the proximal wall communicating with a chamber formed between portions of the upper portion interior surface and the lower portion interior surface; and utilizing the 3-dimensional printer to lay down sequential layers of a separator including a leading portion, the separator being unitarily formed with one of the upper portion interior surface, the lower portion interior surface, and the interior surface of the proximal wall by at least one point of attachment;

wherein the separator is configured to be separated from the at least one point of attachment, and be moved along at least a portion of the lower portion interior surface and at least a portion of the upper portion interior surface away from the proximal wall to move the upper portion and the lower portion apart from one another into an expanded configuration, a height in the expanded configuration measured away from the proximal wall being greater than the maximum height of the proximal wall.

13. The method of claim 12, wherein titanium powder is used with the 3-dimensional printer to manufacture the unitarily formed expandable spinal implant.

14. The method of claim 12, wherein the separator is separably attached to the one of the upper portion interior surface, the lower portion interior surface, and the interior surface of the proximal wall by at least one point of attachment.

15. The method of claim 14, further comprising providing an insertion tool configured to be inserted through the aperture in the proximal wall, and into contact with the separator to break the separator free from the at least one point of attachment, and move the separator toward the first distal wall portion and the second distal wall portion.

16. The method of claim 12, wherein the upper portion interior surface includes a concave portion, and the lower portion interior surface includes a concave portion.

17. The method of claim 16, wherein the concave portions of the upper portion interior surface and the lower portion interior surface are configured to receive therein portions of the separator, the concave portions inhibiting further movement of the separator along the lower portion interior surface and the upper portion interior surface.

18. A method of manufacturing a unitarily formed expandable spinal implant for implantation in a disc space between two adjacent vertebrae, the method comprising:
utilizing a 3-dimensional printer to lay down sequential layers of an upper portion having an upper portion exterior surface and an upper portion interior surface, at least a portion of the upper portion exterior surface being configured to contact one of the two adjacent vertebrae;
utilizing the 3-dimensional printer to lay down sequential layers of a lower portion having a lower portion exterior surface and a lower portion interior surface, at least a portion of the lower portion exterior surface being configured to contact the other of the two adjacent vertebrae;
utilizing the 3-dimensional printer to lay down sequential layers of a wall extending between the upper portion and the lower portion, a maximum height being measured from the upper portion and through the wall to the lower portion, and an aperture provided in the wall between the interior surface and the exterior surface thereof, the aperture provided in the wall communicating with a chamber formed between portions of the upper portion interior surface and the lower portion interior surface; and
utilizing the 3-dimensional printer to lay down sequential layers of a separator including a leading portion, the separator being unitarily formed with one of the upper portion interior surface, the lower portion interior surface, and the wall by at least one point of attachment;
wherein the separator is configured to be separated from the at least one point of attachment, and be moved along at least a portion of the lower portion interior surface and at least a portion of the upper portion interior surface to move the upper portion and the lower portion apart from one another into an expanded configuration.

19. The method of claim 18, wherein the separator is separably attached to the one of the upper portion interior surface, the lower portion interior surface, and the wall by at least one point of attachment.

20. The method of claim 18, wherein the upper portion interior surface includes a concave portion, and the lower portion interior surface includes a concave portion, and wherein the concave portions of the upper portion interior surface and the lower portion interior surface are configured to receive therein portions of the separator, the concave portions inhibiting further movement of the separator along the lower portion interior surface and the upper portion interior surface.

* * * * *